US012746146B2

(12) United States Patent
Voda

(10) Patent No.: US 12,746,146 B2
(45) Date of Patent: Sep. 29, 2026

(54) PORTABLE URINAL SYSTEM AND METHOD OF USE

(71) Applicant: Matthew Voda, Mont Vernon, NH (US)

(72) Inventor: Matthew Voda, Mont Vernon, NH (US)

( * ) Notice: Subject to any disclaimer, the term of this patent is extended or adjusted under 35 U.S.C. 154(b) by 42 days.

(21) Appl. No.: 18/427,787

(22) Filed: Jan. 30, 2024

(65) Prior Publication Data

US 2024/0252343 A1 Aug. 1, 2024

Related U.S. Application Data

(60) Provisional application No. 63/482,059, filed on Jan. 30, 2023.

(51) Int. Cl.
*A61F 5/455* (2006.01)
*A47K 11/00* (2006.01)
(Continued)

(52) U.S. Cl.
CPC ............ *A61F 5/4556* (2013.01); *A47K 11/00* (2013.01); *A47K 11/08* (2013.01); *A47K 11/12* (2013.01);
(Continued)

(58) Field of Classification Search
CPC ...... A61F 5/441; A61F 5/4405; A61F 5/4556; A47K 11/00; A47K 11/08; A47K 11/12; A61G 9/00; A61G 9/006
(Continued)

(56) References Cited

U.S. PATENT DOCUMENTS 2,999,247 A 9/1961 Kulka
3,533,109 A 10/1970 Kishimoto
(Continued)

FOREIGN PATENT DOCUMENTS

AU 2006322648 A1 6/2007
AU 2015100909 A4 8/2015
(Continued)

OTHER PUBLICATIONS

Warm Y, "Retractable Portable Toilet Pro for Camping, Large Camping Toilet for Adult, Folding Adjustable Height Outdoor Toilet, for Folding Stool, Outdoor Fishing, Camping Hiking", accessed on Jun. 11, 2024, available at: https://www.amazon.com/Warm-Retractable-Portable-Adjustable-Collapsible/dp/B08KH4G8TY?th=1.

(Continued)

*Primary Examiner* — Erin Deery
(74) *Attorney, Agent, or Firm* — The Inventor's Friend Patent Law Firm, P.L.L.C.; Nathaniel A. Wickliffe

(57) ABSTRACT

A portable urinal can be designed for use indoors and outdoors. The portable urinal can have a storage tank for storing urine and can be connected to a urine collector. The urinal can be used by a user for urinating and the tank can seal the stored urine thereby maintaining a hygienic environment. A base station with a pump unit can be coupled to the storage tank for emptying the tank, and an outlet tube can drain the urine from the storage tank to a drain. In various embodiments, the portable urinal and the pump unit can be separate, thus, making the device lightweight and easy to maneuver. In other embodiments, the pump can be attached to the device.

8 Claims, 8 Drawing Sheets

(51) Int. Cl.
*A47K 11/08* (2006.01)
*A47K 11/12* (2006.01)
*A61F 5/441* (2006.01)
*A61F 5/451* (2006.01)
*A61F 5/44* (2006.01)

(52) U.S. Cl.
CPC .......... *A61F 5/4404* (2013.01); *A61F 5/4405* (2013.01); *A61F 5/441* (2013.01); *A61F 5/451* (2013.01)

(58) Field of Classification Search
USPC ................................................ 4/144.1–144.4
See application file for complete search history.

(56) References Cited

U.S. PATENT DOCUMENTS

| | | | | |
|---|---|---|---|---|
| 3,611,457 | A | 10/1971 | Wippich | |
| 3,690,315 | A * | 9/1972 | Chittenden | A61M 1/70 604/129 |
| 3,703,731 | A | 11/1972 | Leiser | |
| 4,828,554 | A * | 5/1989 | Griffin | A61F 5/4405 604/326 |
| 5,285,532 | A * | 2/1994 | Sealy | A47K 11/12 4/144.1 |
| 5,285,535 | A | 2/1994 | Stewart et al. | |
| 5,551,097 | A * | 9/1996 | Short | E03D 13/00 4/144.1 |
| 6,812,856 | B2 | 11/2004 | Heinz et al. | |
| 6,904,621 | B2 | 6/2005 | Otto et al. | |
| 7,200,878 | B2 | 4/2007 | Payne | |
| 7,900,288 | B2 | 3/2011 | Fima | |
| 8,104,106 | B2 | 1/2012 | Anderson | |
| 8,181,284 | B1 | 5/2012 | Parker | |
| 8,650,669 | B1 | 2/2014 | Kolter | |
| 9,027,172 | B2 | 5/2015 | Fima | |
| 9,303,420 | B2 | 4/2016 | van der Linde | |
| 9,909,293 | B2 | 3/2018 | Winter et al. | |
| 10,932,630 | B1 | 3/2021 | Luu | |
| 2003/0048200 | A1 | 3/2003 | Heinz et al. | |
| 2006/0037131 | A1 | 2/2006 | Payne | |
| 2006/0277670 | A1* | 12/2006 | Baker | A61G 9/006 4/144.1 |
| 2007/0028375 | A1 | 2/2007 | Marston | |
| 2009/0113615 | A1 | 5/2009 | Anderson | |
| 2009/0235445 | A1 | 9/2009 | Goldstein | |
| 2010/0058518 | A1 | 3/2010 | Bourgeos et al. | |
| 2012/0066825 | A1 | 3/2012 | Birbara et al. | |
| 2012/0233761 | A1 | 9/2012 | Huang | |
| 2014/0033414 | A1* | 2/2014 | Kolter | A47K 11/12 4/144.3 |
| 2014/0259353 | A1 | 9/2014 | van der Linde | |
| 2016/0095479 | A1 | 4/2016 | Jenkin | |
| 2016/0128524 | A1 | 5/2016 | Poore | |
| 2016/0354268 | A1* | 12/2016 | Fennell | A61G 9/006 |
| 2019/0282043 | A1 | 9/2019 | Luster | |
| 2020/0154960 | A1 | 5/2020 | Le | |
| 2020/0281423 | A1 | 9/2020 | Juc | |
| 2021/0059489 | A1 | 3/2021 | Luu | |

FOREIGN PATENT DOCUMENTS

| | | | |
|---|---|---|---|
| AU | 2017261521 | A1 | 5/2018 |
| BR | 1107462 | A2 | 4/2015 |
| CA | 2402797 | A1 | 3/2003 |
| CA | 2905047 | A1 | 9/2014 |
| CA | 2905047 | C | 11/2016 |
| CH | 709004 | A1 | 6/2015 |
| CN | 2344457 | Y | 10/1999 |
| CN | 2528813 | Y | 1/2003 |
| CN | 1209539 | C | 7/2005 |
| CN | 1314866 | C | 5/2007 |
| CN | 101321485 | A | 12/2008 |
| CN | 201343766 | Y | 11/2009 |
| CN | 101848667 | A | 9/2010 |
| CN | 202298834 | U | 7/2012 |
| CN | 102733466 | A | 10/2012 |
| CN | 103243790 | A | 8/2013 |
| CN | 203452156 | U | 2/2014 |
| CN | 203795536 | U | 8/2014 |
| CN | 204098173 | U | 1/2015 |
| CN | 102733466 | B | 3/2015 |
| CN | 103147499 | B | 4/2015 |
| CN | 104631871 | A | 5/2015 |
| CN | 204456972 | U | 7/2015 |
| CN | 204864226 | U | 12/2015 |
| CN | 205307197 | U | 6/2016 |
| CN | 205907778 | U | 1/2017 |
| CN | 106901641 | A | 6/2017 |
| CN | 107212797 | A | 9/2017 |
| CN | 206591860 | U | 10/2017 |
| CN | 107435363 | A | 12/2017 |
| CN | 107806145 | A | 3/2018 |
| CN | 207194098 | U | 4/2018 |
| CN | 207244763 | U | 4/2018 |
| CN | 107976440 | A | 5/2018 |
| CN | 108042039 | A | 5/2018 |
| CN | 108261134 | A | 7/2018 |
| CN | 108378759 | A | 8/2018 |
| CN | 108433623 | A | 8/2018 |
| CN | 207866717 | U | 9/2018 |
| CN | 208039399 | U | 11/2018 |
| CN | 110093963 | A | 8/2019 |
| CN | 209186575 | U | 8/2019 |
| CN | 110629847 | A | 12/2019 |
| CN | 107435363 | B | 2/2020 |
| CN | 110984321 | A | 4/2020 |
| CN | 210315856 | U | 4/2020 |
| CN | 111257029 | A | 6/2020 |
| CN | 111395479 | A | 7/2020 |
| CN | 210917629 | U | 7/2020 |
| CN | 111568282 | A | 8/2020 |
| CN | 111568283 | A | 8/2020 |
| CN | 111616632 | A | 9/2020 |
| CN | 111699387 | A | 9/2020 |
| CN | 211395881 | U | 9/2020 |
| CN | 211395882 | U | 9/2020 |
| CN | 111759210 | A | 10/2020 |
| CN | 211784328 | U | 10/2020 |
| CN | 110984321 | B | 11/2020 |
| CN | 110295658 | B | 2/2021 |
| CN | 112336615 | A | 2/2021 |
| CN | 212816051 | U | 3/2021 |
| CN | 212913634 | U | 4/2021 |
| DE | 10044544 | A1 | 3/2002 |
| DE | 102008037197 | A1 | 2/2009 |
| EP | 1959806 | A1 | 8/2008 |
| EP | 3225223 | A1 | 10/2017 |
| EP | 3225223 | B1 | 1/2020 |
| EP | 3620596 | B1 | 7/2020 |
| GB | 2129688 | B | 10/1984 |
| GB | 2457056 | A | 8/2009 |
| IN | 2752KOLNP2008 | A | 1/2009 |
| JP | 09140628 | A | 6/1997 |
| JP | 2004261530 | A | 9/2004 |
| JP | 2016521191 | A | 7/2016 |
| JP | 5978017 | B2 | 8/2016 |
| JP | 2018075268 | A | 5/2018 |
| KR | 1020040072518 | A | 8/2004 |
| KR | 200380343 | Y1 | 3/2005 |
| KR | 1020060001827 | A | 1/2006 |
| KR | 100598030 | B1 | 6/2006 |
| KR | 1020060076143 | A | 7/2006 |
| KR | 100707813 | B1 | 4/2007 |
| KR | 100818735 | B1 | 3/2008 |
| KR | 1020100051295 | A | 5/2010 |
| KR | 101030052 | B1 | 4/2011 |
| KR | 20120041927 | A | 5/2012 |
| KR | 101397137 | B1 | 5/2014 |
| KR | 1020140093839 | A | 7/2014 |
| KR | 101469089 | B1 | 11/2014 |
| KR | 101603075 | B1 | 3/2016 |
| KR | 200481718 | Y1 | 11/2016 |

(56) References Cited

FOREIGN PATENT DOCUMENTS

| | | | |
|---|---|---|---|
| KR | 101875736 | B1 | 7/2018 |
| KR | 1020180075878 | A | 7/2018 |
| KR | 101907492 | B1 | 10/2018 |
| WO | 2004029375 | A1 | 4/2004 |
| WO | 2007065218 | A1 | 6/2007 |
| WO | 2009120256 | A2 | 10/2009 |
| WO | 2009120256 | A3 | 12/2009 |
| WO | 2014057342 | A2 | 4/2014 |
| WO | 2014057342 | A3 | 6/2014 |
| WO | 2014143856 | A1 | 9/2014 |
| WO | 2014146307 | A1 | 9/2014 |
| WO | 2022190119 | A1 | 9/2022 |

OTHER PUBLICATIONS

"Eazy Kids Trainer Urinal—Blue", accessed on Jun. 11, 2024, available at: https://www.firstcry.om/eazy-kids/eazy-kids-trainer-urinal-blue/4d24eaeb1c1a3/product-detail.

"Patient Bidet System—Solaticare", accessed on Jun. 11, 2024, available at: https://www.indiamart.com/proddetail/patient-bidet-system-solaticare-22465298455.html.

Shining-Life, "Portable Urinal Bedpans Unisex Urine Bottle Sealable w/Lid Female Travel Urinal", accessed on Jun. 11, 2024, available at: https://www.ebay.com/itm/403582555577?hash=item5df76515b9:g:2sQAAOSwurBiSjua&var=673540609165.

YUMSUM, "YUMSUM Unisex Female or Male Bed Urinal Universal Potty Pee Bottle Collector Travel Toilet 1000ML with Lid and Drain Hose (S, Blue)", accessed on Jun. 11, 2024, available at: https://www.amazon.ca/YUMSUM-Unisex-Female-Universal-Collector/dp/B072SMRJMK.

KIDENO, "3 Colors Baby Urine Rocket Shape Urinal Adult Children Adjustable Vertical Height Adjustable Wall Mounted Pee Training in Portable Toilet Pot", accessed on Jun. 11, 2024, available at: https://www.kideno.com/en/product/3-colors-for-baby-boy-diuretic-rocket-shape-pot-me/.

Jieyang Jinyu Plastic Co., Ltd., "Boy toilet PP Adjustable cute height stereo wall mounted kids training toilet Plastic Cartoon Boy Urinal Adjustable Baby Toilet", accessed on Jun. 11, 2024, available at: https://www.alibaba.com/product-detail/Boy-toilet-PP-Adjustable-cute-height_62508696295.html.

Atlas Sanitation Products B.V., "Mobile Urinal Peeone", pluto urinal, ccessed on Jun. 11, 2024, available at: https://plutourinal.com/product/wheeled-mobile-urinal/.

* cited by examiner

PORTABLE URINAL SYSTEM AND METHOD OF USE

FIELD OF THE INVENTION

The present invention generally relates to the field of urinals. More specifically, the present invention relates to a novel portable urinal device having a separate pump unit for draining stored urine from a urine storage tank.

BACKGROUND OF THE INVENTION

Age is an inevitable truth that cannot be controlled by anyone, and passing age can result in both reduced capabilities to move swiftly and easily, and increased need to urinate during the night. This can result in an increasing need for trips to the bathroom at night that can be dangerous to the individual who awakens stiffly and tries to fumble through a dark room to the bathroom without waking their partner by turning on the light. The trips to the bathroom at night can involve impaired vision, balance, and strength and can make urination a hazardous undertaking. These trips to the bathroom can also result in reduced sleep quality after becoming fully awakened on the cold, noisy, bright, and dangerous trip to the bathroom, and this reduced sleep quality in turn is known to have a negative effect on overall health and happiness.

For a number of people of all ages, limited bathroom accessibility can also be caused by any number of reasons including surgery or sickness. In such cases, the patient and/or elderly need to be lifted over a bedpan. The nature of immobility, the weight of the person, and connected auxiliaries like saline tubes, make it challenging and at times, unsafe to execute a such procedure. Further, any deficiencies in cleanup of the patient afterwards can cause infection leading to expensive medical intervention.

Mankind has been trying to deal with the problems of urine collection and disposal since before the days of the chamber pot, and up until now has not developed a solution for the collection and disposal of human urine that is conveniently portable, easy to use, hygienic, quiet, and odor free. A number of portable solutions exist today, including some that are barely different from the chamber pot. These most basic types, including bedpans and other portable devices, require a flow of urine to be correctly aimed towards an open container under the force of gravity. However, they are prone to the splattering of urine when in use, prone to the build-up of offensive odors over time, and prone to spillage when they are carefully carried to an appropriate place for emptying. Though such devices are portable, they are not suited for bedridden patients since they depend on gravity to transport the urine to the container. Gravity imposes constraints on the positioning of the container which must be placed below the level of the patient. These devices are incapable of leakage-free function when the patient is in a lying-down position. At the other end of the spectrum, a number of devices exist that include various pumps and motors to handle moving urine against gravity, managing odors, emptying urine, etc. However, the addition of various pumps and motors is often only marginally effective at reducing odors and leakage, while also increasing the noise, weight, and power requirements of the devices, and the increase in weight and power requirements detrimentally reduces portability.

Many normal people have mobility issues. Many people, not just people with mobility issues, also find it difficult to go to toilets repeatedly and desire a convenient and portable urinal. Conventional portable urinals cannot restrict smell, and urine storage and hygiene is a problem with such devices. Therefore, there is a need for a device that facilitates self-help urination without the unacceptable result of urine ending up in undesired locations or the escape of undesirable odors.

Conventional portable urinals require a large space for storage and cannot be stored inside cupboards, at corners of room and the like. Homes, nursing homes, hospitals and more require portable urinals that are not only convenient for patients and other users but also are compact in size and easy to transport between places.

Therefore, there exists a long felt need in the art for a portable urinal device that overcomes shortcomings associated with conventional urinal devices. There is also a long felt need in the art for a portable urinal device that maintains hygiene, cleanliness and eliminates problems associated with the collection, storage, transportation, and disposal of urine. Additionally, there is a long felt need in the art for a portable urinal device that is easy to maneuver and is lightweight. Moreover, there is a long felt need in the art for a urinal device that can be used in homes, medical centers and more.

SUMMARY OF THE INVENTION

The portable urinal system described herein overcomes disadvantages of the prior art by providing a system and method for collecting, storing, transporting, and disposing of urine in a way that is silent, convenient to use, hygienic, free from splatter, and odor free, and allows for safe and easy disposal without risk of leakage or unwanted release of urine, and without having to see, smell, or come into contact with the stored urine in any way during the disposal process. Furthermore, it can be used in outdoor environments and environments that are far from plumbing fixtures.

This portable urinal system can also overcome disadvantages of the prior art by providing a portable urinal and a separate base station. The portable urinal can include a collector, a holding tank, a vent, a wheeled chassis, and various connections, valving, etc. The collector can be handheld or mounted to the chassis, and can include a valve that allows urine to flow into the holding tank while preventing the escape of odors. An air vent can allow gas to escape through an air filter in a controlled manner while the valve prevents air that is displaced by urine from escaping without passing through the filter. The base station can include hardware that can allow the base station to be easily connected to the portable urinal so that the urine can be pumped from the holding tank of the portable urinal. The base station can be operatively connected to household plumbing, including plumbing under an existing sink, or can be connected to a toilet, etc.

In an embodiment, a portable urinal system can include a portable urinal, and the portable urinal can include a urine collector adapted to collect urine released from a user, a holding tank, and a one-way valve between the collector and the holding tank, the one-way valve permitting liquid to flow downwards under the force of gravity from the collector into the holding tank, and the one one-way valve prohibiting the flow of air and/or liquid upwards from the holding tank to the collector. The portable urinal can include a fitting on the outside of the tank, wherein the fitting configured to allow fluid to be removed from the holding tank when a drain hose is connected to the fitting. The portable urinal system can include a base station, and the base station can include a drain hose configured to be attached to the fitting of the holding tank so that liquid can be removed from the holding tank through the fitting, and a pump configured to pull liquid from the holding tank through the drain hose, thereby emptying the holding tank without the user needing to pour or otherwise contact the fluid within the tank.

The fitting can be mounted near the top of the holding tank, thereby preventing the fluid from leaking through the fitting. The holding tank can have a substantially vertical orientation, with a height that is approximately 3-5 times the width of the holding tank. The holding tank can have a substantially horizontal orientation, with a width or depth that is approximately 3-5 times the height of the holding tank. The holding tank can include a vent on the holding tank, the vent allowing for displaced air to escape from the holding tank when liquid enters the holding tank, and wherein the vent further comprises an odor adsorbent to prevent unwanted odors from being released. The vent on the holding tank can be removably attached to the fitting on the top of the tank. The portable urinal can include one or more handles that extends substantially upwards in a vertical direction, and can be adapted for a user to transport the portable urinal through tight spaces. The base station can include a drain adaption system.

In an embodiment, a method for using a portable urinal system can include placing a reusable portable urinal in a convenient location for a user to urinate into the portable urinal, urinating into a urine collector of a portable urinal, determining that a holding tank of the portable urinal is ready to be emptied, transporting the portable urinal to a base station without urine leaking from the holding tank during transport, operatively connecting a drainage tube of the base station to a fitting of the portable urinal, using a pump of the base station to pump urine from the holding tank through the drainage tube, thereby emptying the holding tank, and returning the reusable portable urinal to the original location. Urinating into the urine collector can include urinating into the urine collector free from electric pumps or other noisemakers, wherein the urine flows from the urine collector into the holding tank under the flow of gravity, thereby urinating without waking a sleeping partner, and wherein urine odors are prevented from escaping from the tank as urine flows into the tank.

BRIEF DESCRIPTION OF THE DRAWINGS

The invention description below refers to the accompanying drawings, of which:

FIG. 1B is a perspective view of a urine collector, according to an illustrative embodiment;

DETAILED DESCRIPTION

There are a great many possible implementations of the invention, too many to describe herein. Some possible implementations are described below. In the following description, for purposes of explanation, numerous specific details are set forth in order to provide a thorough understanding thereof. It should be clear, however, that the innovation can be practiced without various specific details. In other instances, well-known structures and devices are shown in block diagram form in order to facilitate a description thereof. Various embodiments are discussed hereinafter. It should be noted that the figures are described only to facilitate the description of the embodiments. They are not intended as an exhaustive description of the invention and do not limit the scope of the invention. Additionally, any particular embodiment need not have all the aspects or advantages described herein. Thus, in various embodiments, any of the features described herein from different embodiments may be combined. It cannot be emphasized too strongly, however, that these are descriptions of implementations of the invention, and not descriptions of the invention, which is not limited to the detailed implementations described in this section but is described in broader terms in the claims.

Figure 1A:
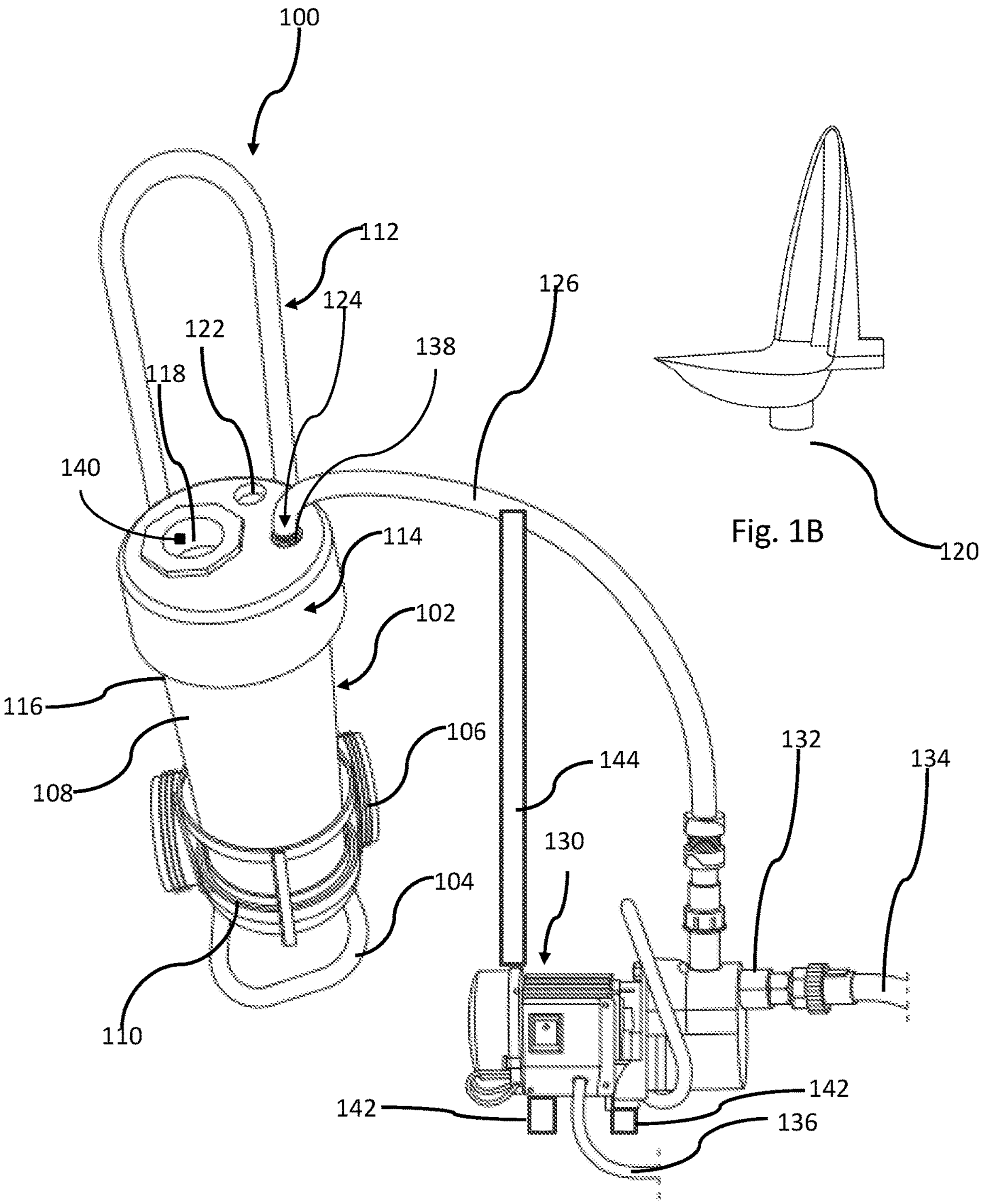
FIG. 1A is a perspective view of portions of a portable urine management system, according to an illustrative embodiment.

FIG. 1A is a perspective view of portions of a portable urine management system, according to an illustrative embodiment. Various embodiments of the portable urine management system 100 can be designed to be used in both indoors and outdoors and are ideal for use in bedrooms, hospitals, nursing homes, and more. A portable urine management system 100 can include a portable urinal 102 and a separate base station 130. The portable urinal 102 can be transported to narrow places for use by people having limited mobility. The portable urinal 102 can include a mobile chassis 110 that carries and supports the portable urinal and allows the urinal to be moved conveniently. Chassis 110 can include a cart 104 that can have 360-degree rotating casters or wheels 106 allowing the portable unit 102 to easily slide and transport between places. Different embodiments of the present invention can have two wheels or four wheels depending on design of the portable urinal 102, but various numbers of wheels are contemplated in the present disclosure, depending on the how and where the portable urinal will be used. In various embodiments, a chassis can have no wheels, and can have skis or glides on the bottom that can allow the chassis to slide across a floor.

A urine storage tank 108 can be accommodated and secured to the chassis 110, and can store urine collected from a user. In various embodiments, the tank 108 may be adapted to hold various quantities of urine depending on the intended usage. A bedside model for a single user that is adapted to be easily moved throughout a cluttered home environment may have a capacity of a few quarts, while a larger model adapted for concerts, construction sites, or other places where urine may be collected from a large number of people may be adapted to store 100 gallons or more.

In the case of a bedside model or other embodiments adapted for use in a cluttered home environment, it can be advantageous for tank 108 to have a vertical orientation. This allows for the portable urinal to have a narrow form that can maneuver easily through cluttered environments while also holding the weight of a full tank nearest to the base of the chassis, thereby making the unit more stable and easily maneuverable. This can allow the unit to slip between pieces of furniture or be parked in small areas. The smaller footprint that comes from the vertical orientation of the wheeled chassis and tank also allows for a user to wheel the portable urinal into small bathrooms to be drained without the user tripping over the portable urinal in the small space.

Having the weight near the base of the chassis makes the unit bottom-heavy which gives the unit a lower center of gravity and makes it more stable and less likely to tip over when it is being moved or if it is bumped into. In various embodiments, the tank can have a height that can be approximately 3-5 times the width, although various dimensions are possible. The tank can also be opaque to prevent visibility of the contents stored within. The chassis can have an ergonomic handle 112 for moving it with little effort by a user. In various embodiments, the handle can extend upwards to reduce the space required to store the device, with the entire portable urinal having a mostly vertical orientation so that it fits easily in a corner. Because all of the openings are at the top of the tank, the tank can be tipped over without spilling, and it can be transported at an angle on two wheels while the user pulls the portable urinal behind them.

In various embodiments, the tank 108 can have a removably placed cap 114 positioned at the top end of a tank body 116. The removable cap 114 can allow access to the inside of the tank body for periodic sterilizations, retrieval of dropped objects, etc. The cap 114 can be designed to cover the tank body 116 and may be fastened using one of, a mechanism, not limited to, threads, snap-fit, press-fit, lock, and so forth, and is designed to maintain an air-tight and watertight connection between the lid and the tank body. In various embodiments, the tank body and the tank cap can be made from polyvinyl chloride (PVC), however, various other materials are possible, including other plastics and stainless steel or other metals.

FIG. 1B is a perspective view of a urine collector, according to an illustrative embodiment. The urine collector 120 can be operatively connected to the tank through an inlet port. A user can direct a stream of urine directly into the collector, and the urine can pass from the collector through tubes and valving and into the storage tank. In various embodiments, the collector can have various shapes that can be adapted to be mounted to the chassis for hands-free usage, and/or adapted to be held closely by the user to further reduce the risk of splatter. In various embodiments, the urinal can be made from Vitreous China, Linear low-density polyethylene (LLDPE), an inert plastic with a non-porous surface that inhibits bacterial biofilm growth, or other appropriate materials. In various embodiments, the collector can be mounted to the chassis and can be adjustable to adapt to the needs of users of different heights. A urine collector 120 can have LED lights on or around the collection area, so that a user can easily use the device without needing to turn on the lights in the room in a dark room or wake a sleeping partner.

Turning back to FIG. 1A, the base station 130 can be a separate unit from the portable urinal 102. Base station 130 can include a pump 132 that can pump urine out of the tank 108, through the urine removal tube 126, and out through the outlet tubing 134. Outlet tubing 134 can be held to a drain, or can be plumbed directly into a drain or other household plumbing. The base station 130 can be easily positioned at a secure and unobstructed area such as under a basin, at a corner of a room and more. In the preferred embodiment, the pump 132 is an electric pump but can also be manual in other embodiments. The pump 132 can be a Marine/RV greywater pump that can be adapted for handling dirt, gels, oils, nitrates, and phosphates, or can be a manual pump, including a foot or hand operated pump.

The separation of the portable urinal 102 and the base station 130 eliminates the need to run a power cord 136 across the floor to power the pump 132, thereby preventing a trip and/or yank hazard. The weight of the pump 132, the power cord 130, and the urine removal tube 126, can be part of the static base station that can rest on the floor, be mounted inside a bathroom cabinet, etc. The base station can be installed in a safe location that eliminates transporting the weight of the pump and other equipment and eliminates the tripping hazard of the cord. The base station can be plumbed directly into the household plumbing, thereby allowing for the clean and hygienic removal of the urine without the urine being handled, seen, or smelled by the user.

Placing the pump on a separate base station away from the portable urinal reduces the weight and size of the portable urinal, lowers the center of gravity, and increases the overall stability of the portable urinal. This arrangement reduces the effort/strength of the user in moving the portable urinal 102. This arrangement also simplifies the weight distribution of items on the portable urinal 102, resulting in a more balanced portable urinal that is less likely to tip over and is easier to steer while moving through space. Furthermore, reducing the weight of the portable urinal when it is empty means that the portable urinal can carry a larger volume of urine before reaching an unwieldy weight.

Placing the pump on a separate base station away from the portable urinal can also reduce the impact of the pump's vibrations on the portable urinal. Typical fluid pumps can generate significant noise and vibration, and locating the pump on a separate base station can reduce the negative effects of the vibration. Locating the pump on a separate base station allows the pump to be in operative contact with solid, stable ground, so that vibration forces are not acting on potentially damageable components of the portable urinal, household furniture, etc. Furthermore, the base station can include vibration reduction pads 142 between the pump and the ground, which can further reduce the vibration felt by the portable urinal while the portable urinal is being drained by the nearby pump. Reducing the vibration on the portable urinal can reduce the risk of numerous negative effects of vibration, including risk of tipping, damage to various connections such as electrical and plumbing connections, sloshing and splashing of liquid in the tank, loosening of screws or fasteners, and wear and tear of wheel axles or casters. In addition to reducing risks such as tipping due to vibration, the reduction of vibration on the portable urinal also reduces noise. Vibration acting on a hollow storage tank can be transmitted and sonically amplified by the hollow cavity, resulting in amplified pump noises, and reducing the vibration on the storage tank can significantly reduce the noise.

Furthermore, the reduction in vibration on the portable urinal may help to limit the release of odors from the portable urinal. The portable urinal includes a 1-way valve the prevents the release of airborne odors through the inlet, and an air filter that can significantly limit the release of airborne odors through the air vent. However, the reduction in vibration can further reduce the existence of airborne odors by reducing the number of odor particles that cross the liquid-air boundary to become airborne odor particles within the storage tank. Vibration of the liquid within the tank results in more particles becoming airborne, whereas reduction of the vibration on the liquid within the tank reduces the number of particles becoming airborne.

The urine removal tube 126 can be connected to the portable urinal using a quick-connect fitting 138 that prevents air from escaping while the urine removal tube is not connected to the portable urinal. This allows the portable urinal to be moved through any environment without cords, tubes, etc. It should be appreciated that a single base station 130 can be releasably coupled to different portable urinals 102, allowing different designs of the portable urinal 102 to be used indoors or outdoors, and allowing multiple portable urinals to be serviced by a single base station, such as in a hospital or nursing home. A base station 130 can include a tube cradle 144 that can hold the tube 126 in an elevated position. Keeping the tube in an elevated position can help to ensure that all liquid is pumped out of the drain hose, or put another way, the tube elevation limits the amount of liquid that may be left in the tube after pumping. Furthermore, although the drain tube 126 has leak-preventing fittings, keeping the tube 126 elevated can help to ensure that any remaining unpumped liquid does not drip onto the floor. Keeping the tube 126 in an elevated position off of the ground can also make it easier for a user to connect the urine removal tube 126 to the portable urinal without the user needing to bend over and pick up the tube 126 off of the ground.

In various embodiments, a portable urinal can have robotic features so that the portable urinal can sense when the urinal is becoming full and can travel independently to the base station and connect to the base station. The robotic urinal can sense when it is full, travel to the base station, empty itself, and return back to the location where it is used, all without the user needing to get up or empty the urinal manually. The robotic portable urinal can connect to the base station so that urine can be pumped away automatically without the user needing to manually transport the portable urinal through the house. In various embodiments, a robotic urinal may respond to voice commands, including commands to empty the urinal or for the urinal to approach the user. In various embodiments, a robotic portable urinal can check for various biomarkers in the urine so that the user and/or the user's healthcare provider can be alerted to any potential health risks. A sensor 140 can be a chemical sensor, optical sensor, or other sensor that can detect biomarkers that may indicate health issues. The robotic portable urinal can then have an indicator on the robotic portable urinal itself and/or can send a message such as a text message or email to the user and/or the user's healthcare provider.

FIG. 2 is a perspective view of the top of a storage tank, according to an illustrative embodiment. The tank 108 can have several ports, such as ports 118, 122, and 124. An inlet port 118 allows urine from the collector to enter the tank, outlet port 124 allows urine to be pumped out of the tank, and an air vent 112 allows air that is displaced by the inflow of urine to escape in a hygienic and odor free manor through an air filter. Although the embodiment in FIG. 1A is shown with a separate port for each function, it should be clear that in various embodiments the number of ports may be combined or reduced. By way of non-limiting example, the air vent can include a removable component that can be attached to the outlet port, so that a single port can perform multiple functions. The ports can all be positioned at the top of the tank to reduce the likelihood of leaking because all urine is contained below the level of the ports. A urine removal tube 126 can connect to the quick connect fitting 138 at the outlet port 124, so that the urine removal tube is connected to the drain pipe 220. Drain pipe 220 can extend all the way down to the bottom of the tank so that the urine can be pumped out through the top of the tank. This eliminates the concern of leaky connections found in other prior art devices by allowing the entire tank to be sealed and free from joints or connectors with the exception of the connections at the top where there is no fluid. The ports can also include port walls 130 that extend below the top surface of the tank. The port walls 130 increase the contact surface area between the tank and the inlet and outlet tubes, thereby strengthening the connections, without requiring an increased thickness in the tank itself. The increased contact surface area and increased strength in the connections reduces the likelihood of failure and leakage.

Figure 2B:
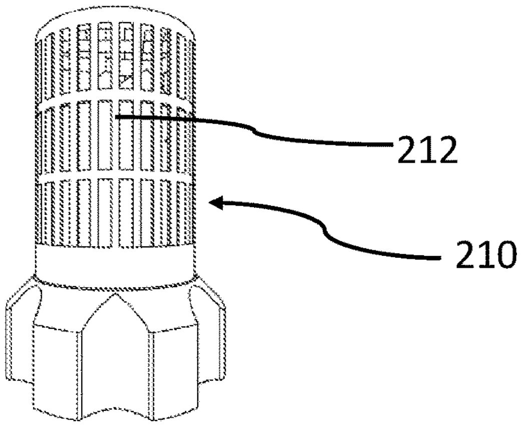
FIG. 2B is a perspective view of an air filter for an air vent, according to an illustrative embodiment.
Figure 2A:
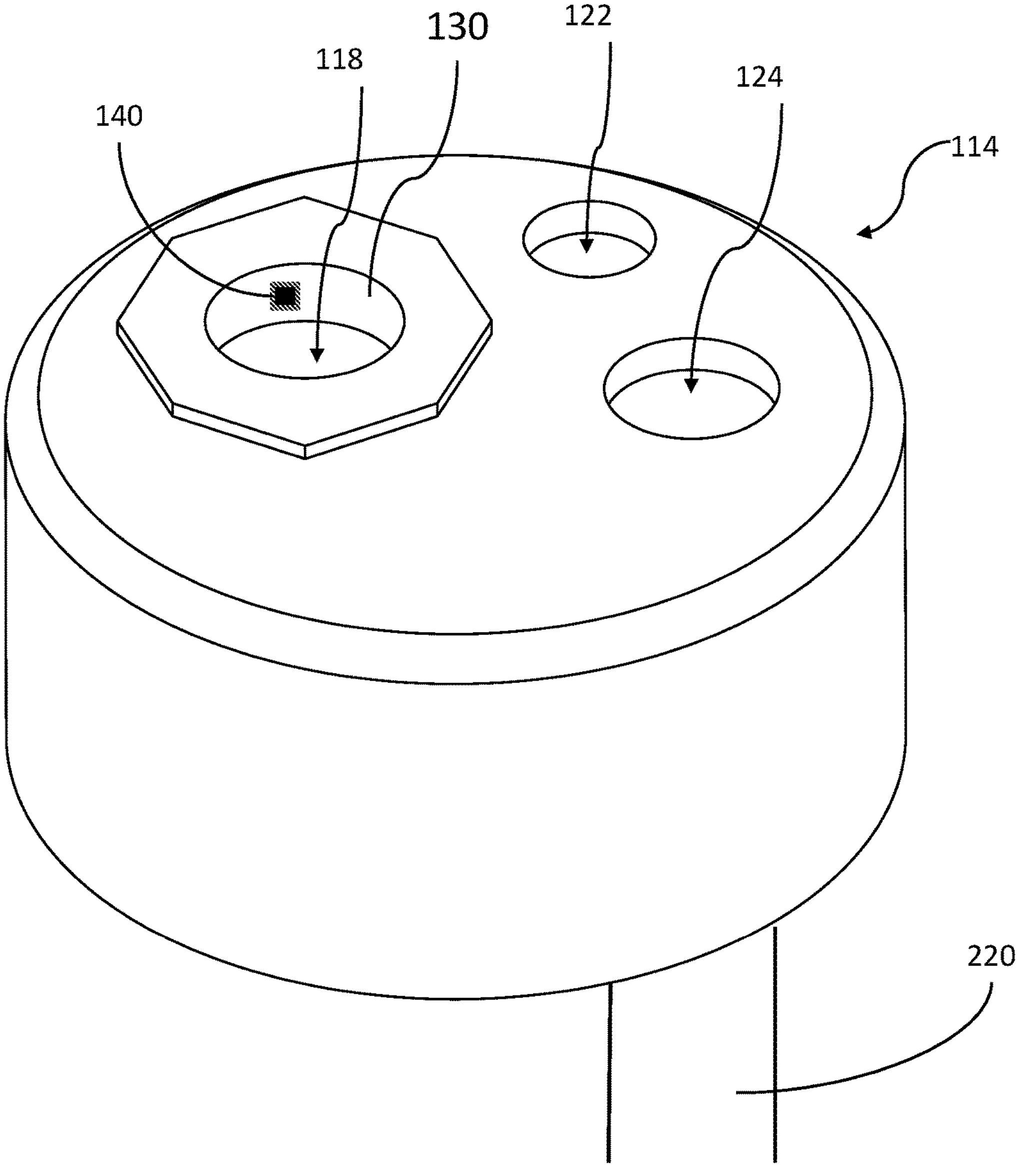
FIG. 2A is a perspective view of the top of a storage tank, according to an illustrative embodiment.

FIG. 2B is a perspective view of an air filter for an air vent, according to an illustrative embodiment. Turning to FIGS. 2A and 2B, air vent port 122 on the top section 114 can be used for venting displaced tank air from the storage tank. The air in the tank is likely to have an unpleasant odor emanating from the urine stored in the storage tank. As urine flows into the tank, a corresponding volume of air is forced out of the tank. An air filter 210 can be operatively connected to air vent port 122 so that air is allowed to escape in a controlled manner through an air filter to eliminate odors. Air filter 210 can contain Zeolite 212 to scrub odors from the passing air. Vinegar or other acids can be added to the tank to lower the pH so that enzymes that emit ammonia can be deactivated, thereby further reducing odor. Eliminating odor allows the portable urinal to be used in a bedroom or other settings, and particularly in settings where a spouse or other people may be sleeping in the same room and would be offended by the smell of odors escaping from the storage tank. In various embodiments, air filter 210 can be connected to a dedicated air vent port, or air filter 210 can be removably connected to a port such as the outlet port. The air filter 210 can be removed so that the port can also be used for an additional function, such as pumping out the urine from the holding tank. Air filter 210 can prevent odors from escaping through a port such as the outlet port, while also allowing displaced air to escape from the holding tank without releasing odors from the tank. In various embodiments, air filter 210 can be connected directly to the tank via screw fittings, snap fittings, or other attachment means. In various embodiments, air filter 210 can be connected to the tank by hose or other tubing, and can be positioned in any number of possible locations including the top of the tank, on the handle, or the side of the tank.

Figure 3B:
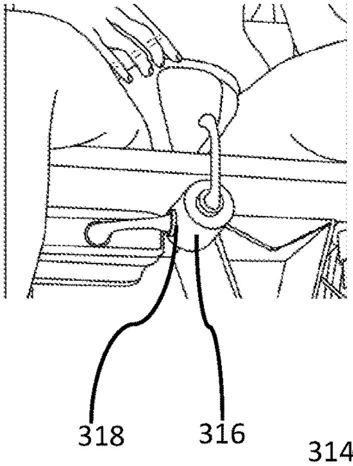
FIG. 3B is an enlarged view of the portable urinal of FIG. 3A, according to the illustrative embodiment.
Figure 3A:
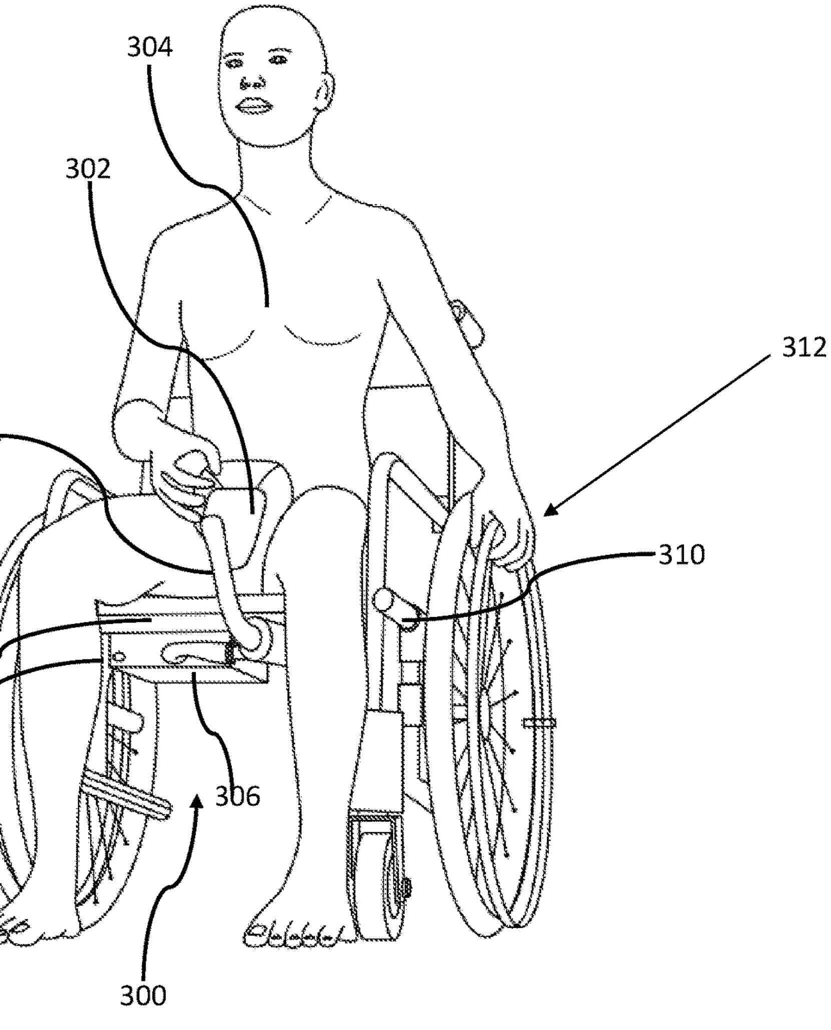
FIG. 3A is a perspective view of a user using a portable urinal adapted to be mounted to a wheelchair and used while seated, according to an illustrative embodiment.

FIG. 3A is a perspective view of a user using a portable urinal adapted to be mounted to a wheelchair and used while seated, according to an illustrative embodiment, and FIG. 3B is an enlarged view of the portable urinal of FIG. 3A, according to the illustrative embodiment. The wheelchair adapted portable urinal 300 is designed to be used by wheelchair bound patients. The urinal 300 has a genital vacuum interface 302 designed to be positioned over genitals of a patient 304. In various embodiments, a genital vacuum interface can be designed for use by men or woman, or can be designed for use by everyone. A tank 306 positioned and attached to the bottom surface 308 of seat 310 of the wheelchair 312 is connected to the interface 302 through a hose 314. The tank 306 has a compact size and may hold approximately 2 L of urine, although different capacities are possible. The tank 306 is positioned in alignment with sitting of the patient 304, thereby aligning the tank 306 with the patient's center of gravity.

A pump 316 can be used for creating a suction through the hose 314 for pulling the urine through the hose 314 into the tank 306. Pump 316 can pull liquid into the storage tank and can also pull air through the interface to maintain a dry environment. The pump 316 can be associated with a pressure sensor 318 that enables activation of the pump 316 and keeps the pump running after urination is complete so that the movement of air can ensure dryness. The pump can remain on for suction to collect even residual urine thus keeping the patient 304 and the interface 302 dry. The tank 306 can have the capacity to hold a day's worth of urine for normal people. Quick-connect fitting 314 can connect the wheelchair adapted portable urinal 300 to the base station for emptying.

The interface 302 can be made of hydrophobic and soft material including but not limited to silicon, rubber, plastic and more. The wheelchair bound urinal device 300 is easy to use by both males and females and allows a user to urinate while sitting in the wheelchair 312. The device 300 is useful for hospitals, nursing homes and community care centers, and can be used by users who are in a seated position or a supine position. The device is more comfortable than a catheter, does not create disposable garbage like a Diaper, and is more clean, comfortable, and sanitary than either one.

Figure 3C:
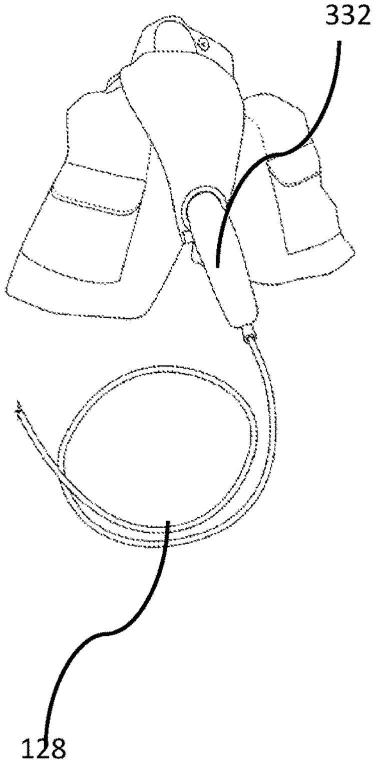
FIGS. 3C, 3D, and 3E are perspective views of urine collectors designed to be worn by male users, according to illustrative embodiments.
Figure 3D:
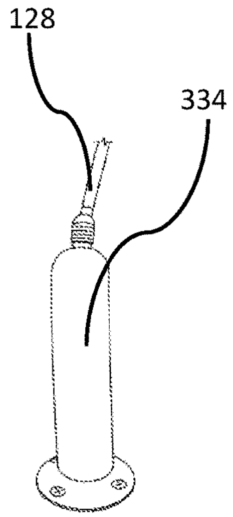
Figure 3E:
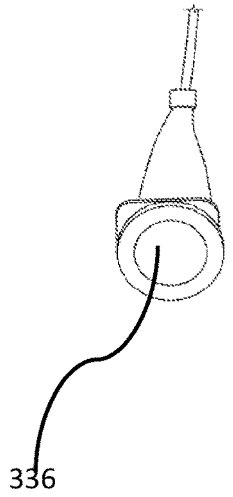

FIGS. 3C, 3D, and 3E are perspective views of urine collectors designed to be worn by male users, according to illustrative embodiments. Urine collectors 332, 334, and 336 can be worn by male users who are wheelchair bound or bed ridden so that urine can be collected without the need for the patient to get up or be moved. Connector tube 128 can connect between the urine collector and the storage tank 306.

Figure 3F:
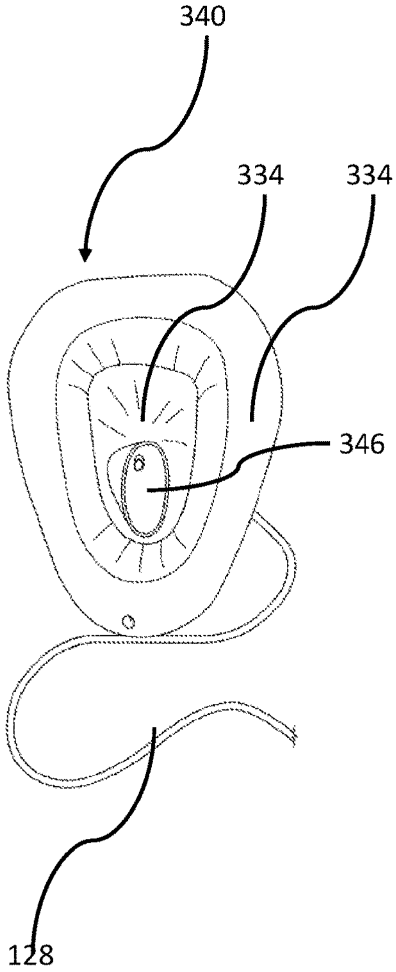
FIG. 3F is a perspective view of an inflatable urine collector that can be used by men or women, in seated or supine positions, according to an illustrative embodiment.

FIG. 3F is a perspective view of an inflatable urine collector that can be used by men or women, in seated or supine positions. The inflatable urine collector 340 can include a flexible dam 342, and flexible dam 342 can be held open and taut by an inflatable rim 344. Inflatable rim 344 can hold the dam open in position to capture all urine. Inflatable rim 344 can also create a soft and flexible interface that can be held comfortably against the skin of the user to create a watertight seal. The inflatable urine collector 340 can also have a drain 346 that can allow the urine to be removed from the urine collector. In various embodiments, a pump 316 can pull liquids and air through the drain 346 to ensure a dry environment.

Figure 4A:
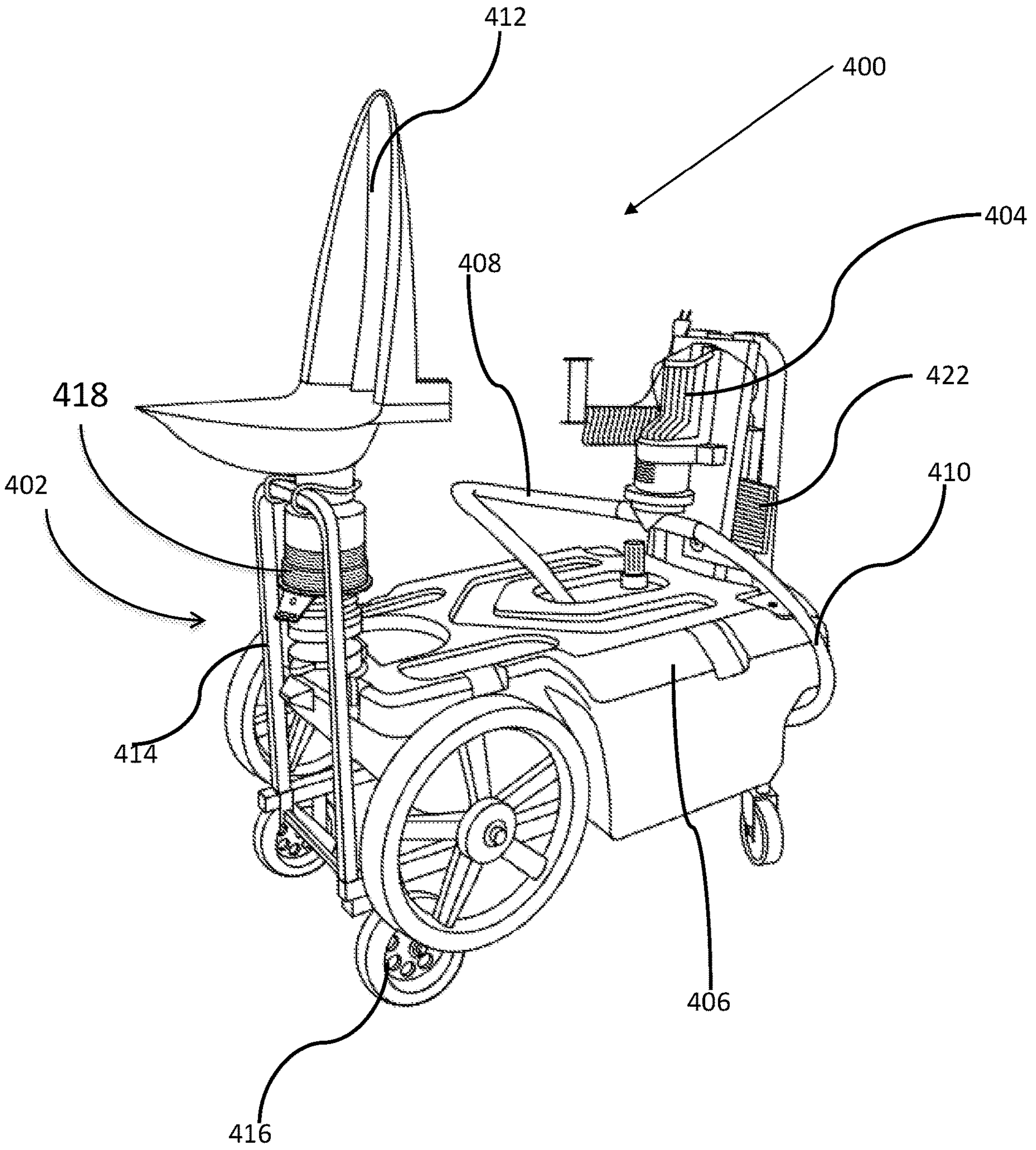
FIG. 4A is a perspective view of a rugged portable urinal that can service multiple users and can be used in outdoor environments, according to an illustrative embodiment.

FIG. 4A is a perspective view of a rugged portable urinal that can service multiple users and can be used in outdoor environments, according to an illustrative embodiment. In various embodiments adapted for outdoor use, the pump 404 can installed onto the main body 402 such that pump 404 and the main body 402 form a single unit construction. The tank 406 and the pump 404 are connected through an inlet piping 408 and an outlet piping 410 from the pump 404 is used for draining the urine from the tank 406.

In embodiments with an onboard pump 404, vibration reduction pads 422 can help to reduce the impact of the pump's vibration on the portable urinal and the storage tank. Typical fluid pumps can generate significant noise and vibration, and the use of vibration reduction pads can reduce the negative effects of the vibration while the portable urinal is being drained by the onboard pump. Reducing the vibration on the portable urinal can reduce the risk of numerous negative effects of vibration, which can include risk of tipping, damage to various connections such as electrical and plumbing connections, sloshing and splashing of liquid in the tank, loosening of screws or fasteners, and wear and tear of wheel axles or casters. In addition to reducing risks such as tipping due to vibration, the reduction of vibration on the portable urinal also reduces noise. Vibration acting on a hollow storage tank can be transmitted and sonically amplified by the hollow cavity, resulting in amplified pump noises, and reducing the vibration on the storage tank can significantly reduce the noise.

Furthermore, the reduction in vibration on the portable urinal may help to limit the release of odors from the portable urinal. The portable urinal includes a 1-way valve the prevents the release of airborne odors through the inlet, and an air filter that can significantly limit the release of airborne odors through the air vent. However, the reduction in vibration can further reduce the existence of airborne odors by reducing the number of odor particles that cross the liquid-air boundary to become airborne odor particles within the storage tank. Vibration of the liquid within the tank results in more particles becoming airborne, whereas reduction of the vibration on the liquid within the tank reduces the number of particles becoming airborne.

A removably attached urinal 412 can be adjustably mounted to the frame 414 and is connected to the tank 406 allowing the tank 406 to store the received urine. The main body 402 can have a plurality of casters 416 allowing a user to easily transport the device 400 between places. In various embodiments, the pump 404 may be removably attached to the main body 402 and can be separated in a manner illustrated in FIG. 1 of the present invention.

In various embodiments, it can be advantageous for tank 406 to have a horizontal orientation, which can allow the portable urinal to sit lower to the ground, and allow for a lower center of gravity. In various embodiments, the tank 406 can have a width and/or depth that can be approximately 3-5 times the height of the holding tank. Put another way, a horizontal measurement of the tank can be approximately 3-5 times the vertical measurement of the tank. This can be desirable for female users who sit to use the portable urinal as well as shorter male users. Having a substantially horizontal orientation also increases the stability of the portable urinal. Increased stability can be advantageous in outdoor use, including increased stability while transporting the portable urinal over uneven surfaces and including increased stability in the case of seated female users.

Figure 4B:
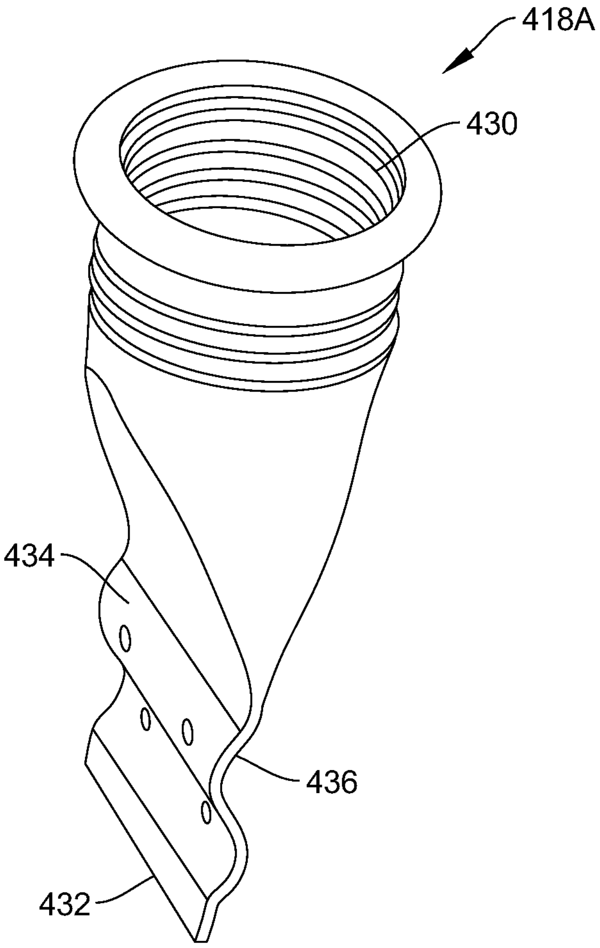
FIG. 4B is a perspective view of a one way valve according to an illustrative embodiment.

A valve 418 can allow urine to flow through the valve and into the tank, but can prevent air from escaping. Valve 418 can remain closed when not in use, and can open as needed when urine is flowing down through the valve. In various embodiments, a valve 418 can be a rubber curtain drain trap, or a ping pong ball style drain valve, or other types of valves that can allow liquid to flow down through the valve but prevent air from escaping upwards through the valve. In various embodiments, a valve 418 can be various backflow preventors, such as valve 418A shown in FIG. 4B. Valve 418A can have an opening 430 at the top with a lower sealing section 432 that has sides 434, 436 pressed together. Fluid entering the opening 430 at the top can create pressure on the lower sealing section 432 that forces sides 434 and 436 to separate, thereby allowing the fluid to pass through the lower sealing section under the force of gravity. In the absence of fluid pressure on the lower sealing section, the sides 434 and 436 will remain tightly sealed together, preventing the escape of unwanted odors. In various embodiments, a valve can be various valves such as the ones described in U.S. Pat. No. 7,900,288, titled DRAIN CAR- TRIDGE HAVING REMOVABLE VALVED SYSTEM and U.S. Pat. No. 9,027,172, titled DRAIN VALVE CORE, the entire disclosures of both of which are incorporated herein by reference. Any specific valves described herein are merely representative samples of possible valves that can be used in the portable urinal described herein. Possible valves for use in the portable urinal do not require flushing, and can operate to prevent the escape of odors and gases while allowing fluid to pass through the valve in one direction only. In various embodiments, the valve can be an integral part of the collector or may be separately positioned between the collector and the tank. The valve can prevent the odor of urine from rising up and out of the portable urinal. Various different valves can be used in any of the various embodiments of portable urinals described herein.

Figure 5:
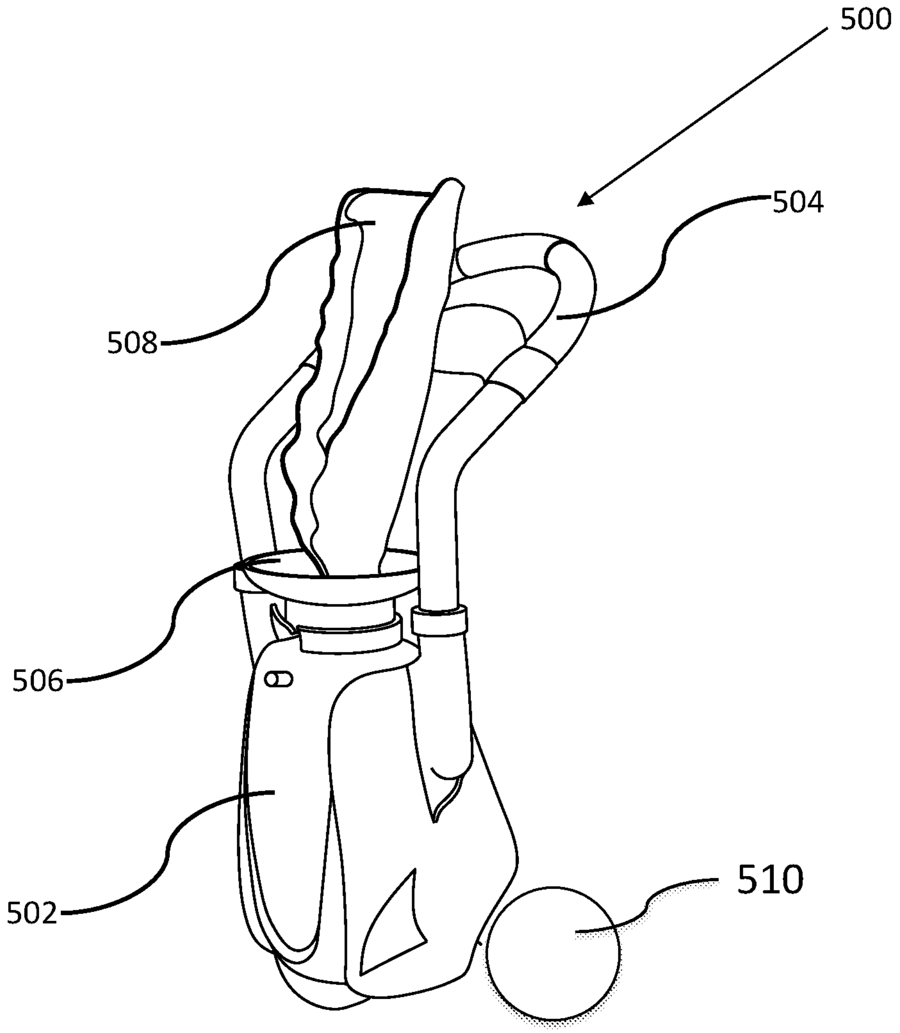
FIG. 5 is a perspective view of a portable urinal adapted for both indoor and outdoor use, according to an illustrative embodiment.

FIG. 5 is a perspective view of a portable urinal adapted for both indoor and outdoor use, according to an illustrative embodiment. Portable urinal 500 can have a tank 502 with an integrated handle 504 and wheels 510. Collector 508 can securely mounted to the top of the portable urinal, and urine can be routed into the tank 502 through the valve 506. Portable urinal 500 can be wheeled into nearly any location, and can be used hands-free. Portable urinal 500 can be used for camping or various other outdoor environments where the use of an indoor bathroom is inconvenient or far away, or would result in mud and dirt being tracked through a house between the outside and the bathroom. It should be clear that various shapes and sizes of portable urinals are possible without departing from the scope of the present application.

Figure 6:
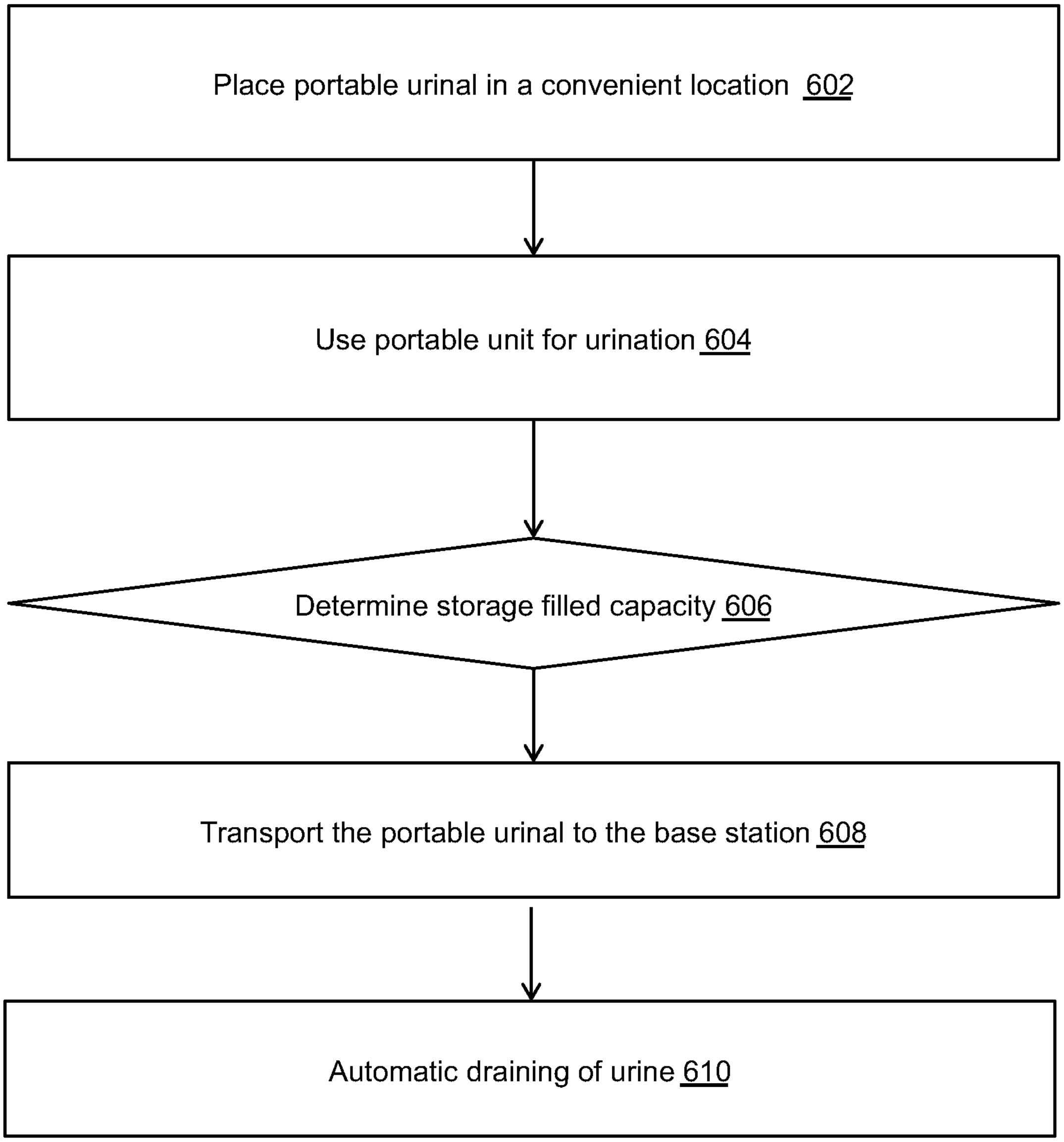
FIG. 6 is a chart showing a method of use for a portable urine management system, according to an illustrative embodiment.

FIG. 6 is a chart showing a method of use for a portable urine management system, according to an illustrative embodiment. At box 602, a user can place a portable urinal near the bedside or other areas where the user would like to be able to urinate without traveling to a bathroom. At box 604, a user can urinate into the urine collector of a portable urinal. At box 606, the user can determine that the volume of urine in the tank has reached a level that should be drained. At box 608, the user can transport the portable urinal to the base station. At box 610, the user can connect the portable urinal to the base station and engage the pump, thereby draining away all urine. The user can also rinse the portable urinal at this time. The user can then proceed to box 602 and can transport the urinal to a convenient location to be reused.

The portable urinal described herein can be adapted for use in nearly any environment, including environments with other people sleeping nearby. The portable urinal can be silent and able to operate without the need for a pump or other noisy equipment, while also preventing the escape of unwanted odors into the environment. As urine flows silently downward into the tank under the flow of gravity, escaping air flows outwards silently through the air filter to eliminate odors. The portable urinal can be easily maneuverable through nearly any environment with no risk of spillage or leakage. Connecting the portable urinal to a base station for pumping in a closed system prevents the possibility that urine may be spilled or otherwise result in unwanted urine release into the environment. The closed system also prevents odors from being released when the storage tank is being emptied.

It should be clear that the portable urinal described herein can be of any suitable size and configuration as is known in the art without affecting the overall concept of the invention, provided that it accomplishes the above stated objectives. One of ordinary skill in the art will appreciate that the portable urinals shown in the figures are for illustrative purposes only, and that many other sizes and shapes of the portable urinal are well within the scope of the present disclosure. Although the dimensions of the portable urinal are important design parameters for user convenience, the portable urinal may be of any size that ensures optimal performance during use and/or that suits the user's needs and/or preferences.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. Accordingly, this description is meant to be taken only by way of example, and not to otherwise limit the scope of this invention.

The invention claimed is:

1. A portable urinal system comprising:

a portable urinal, the portable urinal comprising:

- a urine collector adapted to collect urine released from a user;
- a holding tank;
- a one-way valve between the collector and the holding tank, the one-way valve permitting liquid to flow downwards under the force of gravity from the collector into the holding tank, and the one-way valve prohibiting the flow of air or liquid upwards from the holding tank to the collector;
- a fitting on the outside of the tank, the fitting configured to allow fluid to be removed from the holding tank when a drain hose is connected to the fitting; and a base station, the base station comprising:

- the drain hose, the drain hose configured to be attached to the fitting of the holding tank so that liquid can be removed from the holding tank through the fitting; and
- a pump configured to pull liquid from the holding tank through the drain hose, thereby emptying the holding tank without the user needing to pour or otherwise contact the fluid within the tank.

2. The portable urinal system of claim 1, wherein the fitting is mounted near a top of the holding tank, thereby preventing the fluid from leaking through the fitting.

3. The portable urinal system of claim 1, wherein the holding tank has a substantially vertical orientation, with a height that is approximately 3-5 times the width of the holding tank.

4. The portable urinal system of claim 1, wherein the holding tank has a substantially horizontal orientation, with a width or depth that is approximately 3-5 times the height of the holding tank.

5. The portable urinal system of claim 1, wherein the holding tank further comprises a vent on the holding tank, the vent allowing for displaced air to escape from the holding tank when liquid enters the holding tank, and wherein the vent further comprises an odor adsorbent to prevent unwanted odors from being released.

6. The portable urinal system of claim 5, wherein the vent on the holding tank is removably attached to a fitting on a top of the tank.

7. The portable urinal system of claim 1, the portable urinal further comprising one or more handles that extends substantially upwards in a vertical direction, and is adapted for a user to transport the portable urinal.

8. The portable urinal system of claim 1, wherein the base station further comprises a drain adaption system.

* * * * *